US008083681B2

(12) United States Patent
Kadokura

(10) Patent No.: US 8,083,681 B2
(45) Date of Patent: Dec. 27, 2011

(54) ULTRASONIC PROBE

(75) Inventor: Masahiko Kadokura, Sagamihara (JP)

(73) Assignee: Panasonic Corporation, Osaka (JP)

( * ) Notice: Subject to any disclaimer, the term of this patent is extended or adjusted under 35 U.S.C. 154(b) by 1016 days.

(21) Appl. No.: 10/534,961

(22) PCT Filed: Dec. 22, 2003

(86) PCT No.: PCT/JP03/16489
§ 371 (c)(1),
(2), (4) Date: May 16, 2005

(87) PCT Pub. No.: WO2004/058073
PCT Pub. Date: Jul. 15, 2004

(65) Prior Publication Data
US 2006/0074316 A1    Apr. 6, 2006

(30) Foreign Application Priority Data
Dec. 24, 2002    (JP) ................. 2002-372864

(51) Int. Cl.
*A61B 8/14*    (2006.01)
(52) U.S. Cl. ....................... 600/459; 600/462
(58) Field of Classification Search ........... 600/437–463
See application file for complete search history.

(56) References Cited

U.S. PATENT DOCUMENTS

| | | | |
|---|---|---|---|
| 4,841,979 A | | 6/1989 | Dow et al. |
| 4,895,158 A * | | 1/1990 | Kawabuchi et al. .......... 600/463 |
| 5,048,529 A * | | 9/1991 | Blumenthal .................. 600/446 |
| 5,090,414 A * | | 2/1992 | Takano ......................... 600/461 |
| 5,255,684 A * | | 10/1993 | Rello ............................ 600/463 |
| 5,351,692 A | | 10/1994 | Dow et al. |
| 5,450,851 A * | | 9/1995 | Hancock ....................... 600/462 |
| 5,469,852 A | | 11/1995 | Nakamura et al. |
| 5,479,929 A * | | 1/1996 | Cooper et al. ................ 600/459 |
| 5,494,040 A * | | 2/1996 | Nakao et al. .................. 600/463 |
| 5,662,116 A * | | 9/1997 | Kondo et al. ................. 600/462 |
| 5,833,616 A * | | 11/1998 | Gruner et al. ................ 600/462 |
| 6,709,397 B2 * | | 3/2004 | Taylor .......................... 600/459 |
| 6,840,938 B1 * | | 1/2005 | Morley et al. ................. 606/51 |

FOREIGN PATENT DOCUMENTS

| | | |
|---|---|---|
| EP | 0 253 268 | 7/1987 |
| EP | 1 208 800 | 5/2002 |
| GB | 2 082 769 | 3/1982 |
| JP | 2-57242 | 2/1990 |
| JP | 10-174686 | 6/1998 |
| JP | 10-179588 | 7/1998 |
| JP | 2001-161694 | 6/2001 |
| JP | 2001-327499 | 11/2001 |
| JP | 2001-327501 | 11/2001 |

* cited by examiner

*Primary Examiner* — Long Le
*Assistant Examiner* — Sanjay Cattungal
(74) *Attorney, Agent, or Firm* — Hamre, Schumann, Mueller & Larson, P.C.

(57) ABSTRACT

An ultrasonic probe according to the present invention includes an inserting portion to be inserted into a body cavity and a grip portion 1 held by an operator outside of the body cavity. The inserting portion 2 includes a transducer unit 4, a rotation axis provided in the transducer unit 4, and a swing mechanism for swinging the transducer unit 4 around the rotation axis as a center, and the grip portion 1 includes a motor 5 for generating a driving force for driving the swing mechanism. The swing mechanism includes a shaft 9 connected to the motor 5, a first pulley 6 attached coaxially to the shaft 9, a second pulley 7 attached coaxially to the rotation axis of the transducer unit 4, and a wire 8 connecting the first pulley 6 and the second pulley 7.

9 Claims, 4 Drawing Sheets

ULTRASONIC PROBE

TECHNICAL FIELD

The present invention relates to an ultrasonic probe for transmitting and receiving ultrasonic waves to and from a living body by an ultrasonic transducer inserted into a body cavity.

BACKGROUND ART

As a probe configuring an ultrasonic diagnostic apparatus for use in the field of medicine, an intracorporeal insertion type ultrasonic probe for carrying out ultrasonic scanning in a body by inserting an ultrasonic transducer into the body cavity of a subject is known.

FIG. 5 is a schematic cross-sectional view showing a structure of a conventional intracorporeal insertion type ultrasonic probe (hereinafter, referred to as a "first conventional example"). An ultrasonic probe having such a structure is described in JP 2001-327501 A, for example. This probe includes an inserting portion 102 to be inserted into a body cavity and a grip portion 101 held by an operator outside of the body cavity. The inserting portion 102 has an elongate rod shape and includes a transducer unit 103 in the vicinity of an end thereof. The inserting portion 102 further includes a swing mechanism for swinging the transducer unit 103. In the first conventional example, the swing mechanism includes a pair of arm members 104 that are arranged in parallel with each other so as to hold the transducer unit 103 therebetween, a connected arm 105 connected to the arm members 104, and a shaft 107 connected to the connected arm 105 via a bevel gear 106. The grip portion 101 includes a motor 108 for generating a driving force for driving the swing mechanism, the motor 108 being connected to the shaft 107. In such an ultrasonic probe, when the motor 108 is driven, the shaft 107 is rotated around an axis of the inserting portion, and this rotating force is transmitted to the connected arm 105 via the bevel gear 106, so that the connected arm 105 is rotated around an axis (hereinafter, referred to as a "swing axis") orthogonal to the axis of the inserting portion. By the rotation of the connected arm 105, the arm members 104 are advanced and retreated reversely to each other while staying in parallel with each other. As a result, the transducer unit 103 is swung.

However, in the first conventional example, the bevel gear 106 is used as means for converting the rotational movement of the shaft around the axis of the inserting portion into the rotational movement around the swing axis. Therefore, vibrations are likely to be created by contact between gear structures when the swing mechanism is driven. Such vibrations pose a problem of preventing smooth swing movement of the ultrasonic transducer, i.e., smooth ultrasonic scanning, which results in difficulty in obtaining precise ultrasound images.

FIG. 6 is a schematic cross-sectional view showing a structure of another conventional intracorporeal insertion type ultrasonic probe (hereinafter, referred to as a "second convennitonal example"). An ultrasonic probe having such a structure is described in JP 10(1998)-179588 A, for example. This probe includes the inserting portion 102 having the transducer unit 103 and the grip portion 101 having the motor 108 as in the first conventional example. In the second conventional example, the swing mechanism for swinging the transducer unit includes a driving pulley 109 connected to a rotation axis of the motor 108, a driven pulley 111 connected to a swing axis 110 of the transducer unit 103, and a wire 112 connecting these pulleys. In such an ultrasonic probe, when the motor 108 is driven, the driving pulley 109 is rotated, and accordingly the wire 112 is moved. The movement of the wire 112 rotates the driven pulley 111, and then the transducer unit 103 connected to the driven pulley 111 is swung.

As described above, in the second conventional example, the swing mechanism configured by the pulleys and the wire is used. However, since the wire 112 connects the driving pulley 109 provided at the motor 108 in the grip portion 101 and the driven pulley 111 provided at the transducer unit 103 at an end of the inserting portion 102, the wire 112 needs to be long. Accordingly, the wire is likely to become loose, resulting in displacement of the driven pulley, and furthermore displacement of the ultrasonic transducer connected to the driven pulley. Such displacement also makes it difficult to obtain precise ultrasonic images.

DISCLOSURE OF INVENTION

It is an object of the present invention to provide an ultrasonic probe that allows precise ultrasonic images to be obtained by swinging an ultrasonic transducer smoothly and reducing displacement of the ultrasonic transducer.

In order to achieve the above-mentioned object, an ultrasonic probe of the present invention includes an inserting portion to be inserted into a body cavity; and a grip portion held by an operator outside of the body cavity. The inserting portion includes a transducer unit for transmitting and receiving an ultrasonic wave, a rotation axis provided in the transducer unit, and a swing mechanism for swinging the transducer unit around the rotation axis as a center, and the grip portion includes a motor for driving the swing mechanism. The swing mechanism includes a shaft connected to the motor, a first pulley provided at an end portion of the shaft different from an end portion connected to the motor, a second pulley coaxially provided at the rotation axis, and a wire connecting the first pulley and the second pulley. Rotational movement of the motor is transmitted to the transducer unit via the shaft, the first pulley, the wire, and the second pulley.

BEST MODE FOR CARRYING OUT THE INVENTION

In an ultrasonic probe of the present invention, a driving force generated by a motor in a grip portion is transmitted to a first pulley via a shaft so as to rotate the first pulley, and the rotational movement of the first pulley is transmitted to a second pulley via a wire so as to rotate the second pulley, whereby a transducer unit can be swung. In this manner, the transducer unit is swung by wire drive without the use of a gear, which makes it possible to reduce undesirable vibrations created when a swing mechanism is driven.

Further, the driving force of the motor is transmitted to the swing mechanism in an inserting portion via the shaft and in the swing mechanism, transmitted to the transducer unit by the wire. Therefore, the wire can be made relatively short, which makes it possible to reduce loosening of the wire and thus to reduce displacement of the transducer unit.

In the ultrasonic probe, it is preferable that the first pulley and the second pulley have the same diameter. According to this preferable example, the first pulley and the second pulley have the same rotation angle, which makes it easy to control the swing movement of the ultrasonic transducer.

Further, in the ultrasonic probe, it is preferable that the wire is moved in a direction orthogonal to a direction of a rotation axis of the first pulley on a peripheral surface of the first pulley, and moved in a direction orthogonal to a direction of a rotation axis of the second pulley on a peripheral surface of the second pulley. According to this preferable example, it is possible to suppress sliding of the wire in a direction of a rotation axis of the pulleys on a peripheral surface of the pulleys.

Further, in the ultrasonic probe, it is preferable that the shaft and the transducer unit are provided so that a direction of a rotation axis of the shaft is orthogonal to a direction of the rotation axis of the transducer unit, and in the swing mechanism, the direction in which the wire is moved is changed perpendicularly between the first pulley and the second pulley. According to this preferable example, it is possible to suppress sliding of the wire in the direction of the rotation axis of the pulleys on the peripheral surface of the pulleys.

In order to realize the above-mentioned preferable example, the swing mechanism may include a third pulley for changing perpendicularly the direction in which the wire is moved.

Further, in the ultrasonic probe, it is preferable that a groove in which the wire is positioned is formed on the peripheral surface of the first pulley and the second pulley. According to this preferable example, it is also possible to suppress sliding of the wire in the direction of the rotation axis of the pulleys on the peripheral surface of the pulleys.

Hereinafter, an embodiment of the present invention will be described with reference to the drawings.

Figure 1:
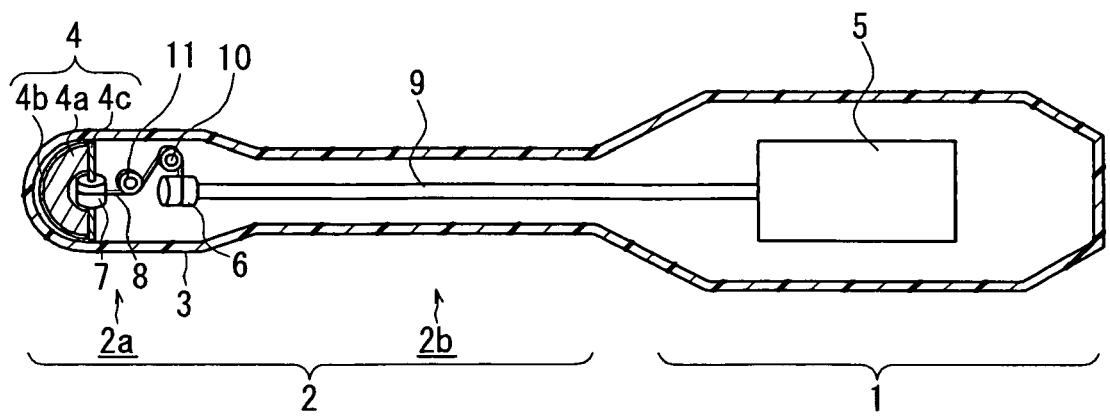
FIG. 1 is a schematic cross-sectional view showing an example of a structure of an ultrasonic probe according to the present invention.

FIG. 1 is a schematic cross-sectional view showing an example of the ultrasonic probe of the present invention. This ultrasonic probe includes an inserting portion 2 to be inserted into a body cavity and a grip portion 1 held by an operator outside of the body cavity.

The grip portion 1 includes a motor 5 for generating a driving force for driving a swing mechanism described later. Although not shown in the figure, the grip portion 1 further includes a motor control system for controlling a rotation angle, rotation direction, rotation speed, and the like of the motor 5. Further, although not shown in the figure, a cable is led out from the grip portion 1 so as to connect the ultrasonic probe with an ultrasonic diagnostic apparatus main body.

The inserting portion 2 includes an ultrasonic transducer housing portion 2a provided at an end portion thereof and a rod portion 2b for locating the ultrasonic transducer housing portion 2a at a desirable position in the body cavity.

In the inserting portion 2, a transducer unit 4 is stored in the ultrasonic transducer housing portion 2a. The transducer unit 4 includes an ultrasonic transducer 4b, a holder 4a for holding the ultrasonic transducer 4b, and a support axis 4c for supporting the holder 4a. The support axis 4c is supported in a freely rotatable manner by bearings (not shown) provided on an inner wall surface of a housing 3 of the ultrasonic transducer housing portion 2a, at both end portions thereof. This allows the ultrasonic transducer 4b held by the holder 4a to be swung in conjunction with the rotation of the support axis 4c with the support axis 4c as an axis.

Further, although not shown in the figure, in the transducer unit 4, an acoustic lens is provided so as to be opposed to a surface for transmitting and receiving ultrasonic waves of the ultrasonic transducer 4b, an acoustical coupling medium is filled in the space between the ultrasonic transducer 4b and the acoustic lens, and a backing layer for absorbing ultrasonic waves is provided on the back of the surface for transmitting and receiving ultrasonic waves of the ultrasonic transducer 4b. From the transducer unit 4, a plurality of signal lines for transmitting and receiving electric signals to and from the ultrasonic transducer are led out. These signal lines are introduced into the grip portion 1 via the rod portion 2b.

Figure 2A:
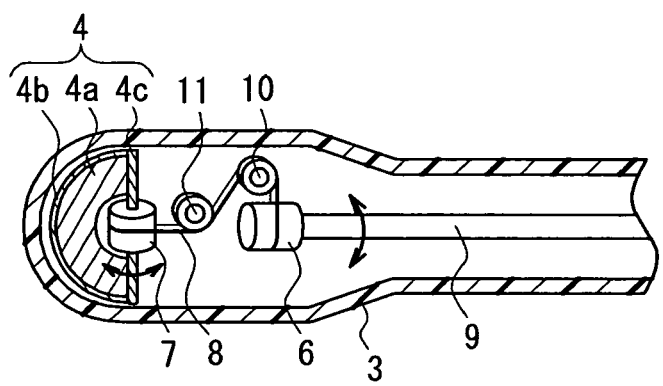
FIG. 2A is a schematic view for explaining an internal structure of an inserting portion of the ultrasonic probe.
Figure 2B:
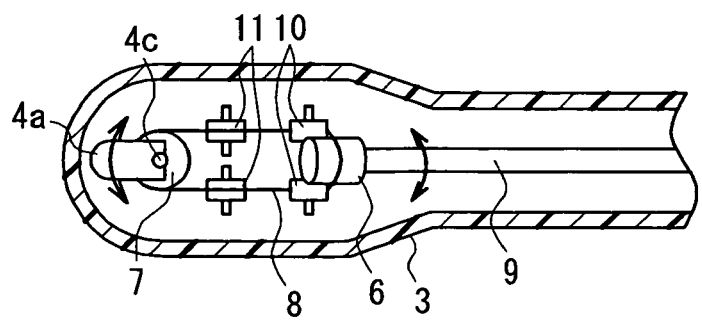
FIG. 2B is a schematic view for explaining the internal structure of the inserting portion of the ultrasonic probe.

The inserting portion 2 further includes a swing mechanism for swinging the transducer unit 4. FIG. 2A is a schematic cross-sectional view showing an example of a structure of the swing mechanism, and FIG. 2B shows the swing mechanism in FIG. 1 viewed from below. This swing mechanism includes a shaft 9 connected to the motor 5, a first pulley 6 attached to an end of the shaft 9, a second pulley 7 attached to the transducer unit 4, and a wire 8 connecting these pulleys.

The shaft 9, which may be, for example, a flexible shaft, is provided in the rod portion 2b. Since the signal lines led out from the ultrasonic transducer are provided in the rod portion 2b as described above, it is preferable that the shaft 9 is provided with a cover so that contact between the shaft 9 and the signal lines is prevented.

On the other hand, the first pulley 6, the second pulley 7, and the wire 8 are provided in the ultrasonic transducer housing portion 2a. The first pulley 6 is attached so that a rotation axis thereof corresponds to a rotation axis (hereinafter, referred to as a "shaft axis") of the shaft 9, and the second pulley 7 is attached so that a rotation axis thereof corresponds to a rotation axis (i.e., the support axis 4c) of the transducer unit 4. The endless (i.e., loop-shaped) wire 8 connects these pulleys in a movable manner. With this configuration, it is possible to rotate the first pulley 6 in conjunction with the rotation of the shaft 9, transmit the rotational movement of the first pulley 6 to the second pulley 7 via the wire 8 so as to rotate the second pulley 7, and rotate (swing) the transducer unit 4 in conjunction with the rotation of the second pulley 7.

It is preferable that the first pulley 6 and the second pulley 7 have the same diameter. Herein, the "diameter" is a diameter of the pulley at a portion where the wire is positioned. For example, in the case where a wire groove is formed on a peripheral surface of the pulley, the diameter of the pulley is a diameter of a cross section of the pulley taken along this groove.

Figure 3:
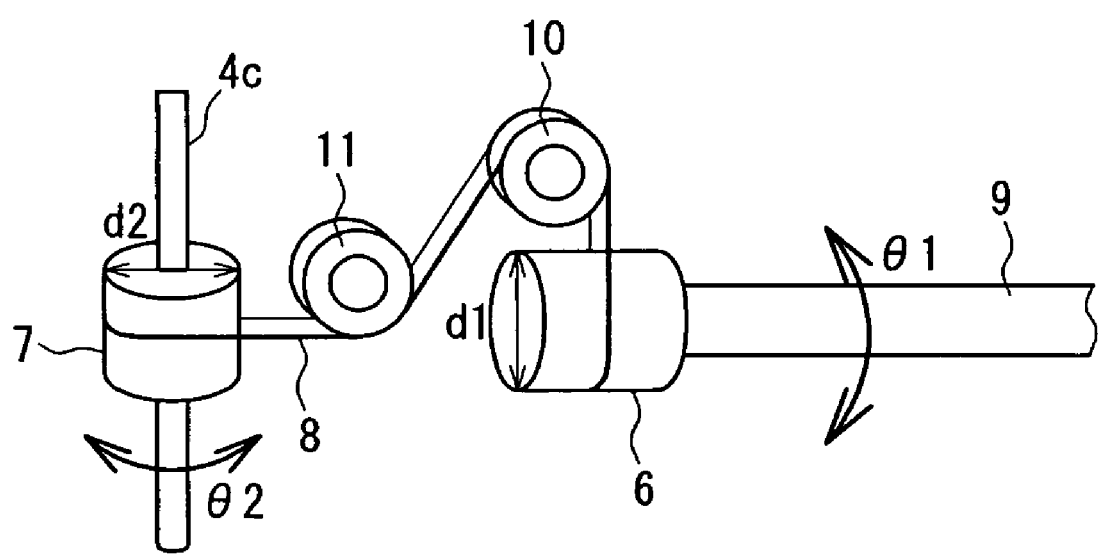
FIG. 3 is a schematic view for explaining the relationship among diameters and rotation angles of first and second pulleys of the ultrasonic probe.

As shown in FIG. 3, when the diameters of the first and second pulleys are d1 and d2, respectively, and the rotation angles of the first and second pulleys are $\theta1$ and $\theta2$, respectively, these values generally satisfy the following relationship: $\theta1 \times d1 = \theta2 \times d2$. Accordingly, when the diameter d1 of the first pulley 6 and the diameter d2 of the second pulley 7 have the same value, the relationship $\theta1 = \theta2$ can be satisfied, which means the rotation angle of the first pulley 6 can be made equal to the rotation angle of the second pulley 7.

For example, in the case where the rotation of the motor 5 is transmitted to the first pulley 6 as it is (i.e., a rotation angle of the motor 5 is the same as the rotation angle of the first pulley 6), and the rotation of the second pulley 7 is transmitted to the transducer unit 4 as it is (i.e., the rotation angle of the second pulley 7 is the same as a rotation angle of the transducer unit 4), when the first pulley 6 and the second pulley 7 have the same rotation angle, the motor 5 and the transducer unit 4 can have the same rotation angle. As a result, it is possible to control the swing movement of the ultrasonic transducer easily with a relatively simple motor control system.

It is preferable that the wire 8 is moved in a direction orthogonal to the rotation axis of the first pulley 6 on the peripheral surface of the first pulley 6 and moved in a direction orthogonal to the rotation axis of the second pulley 7 on the peripheral surface of the second pulley 7.

Figure 4A:
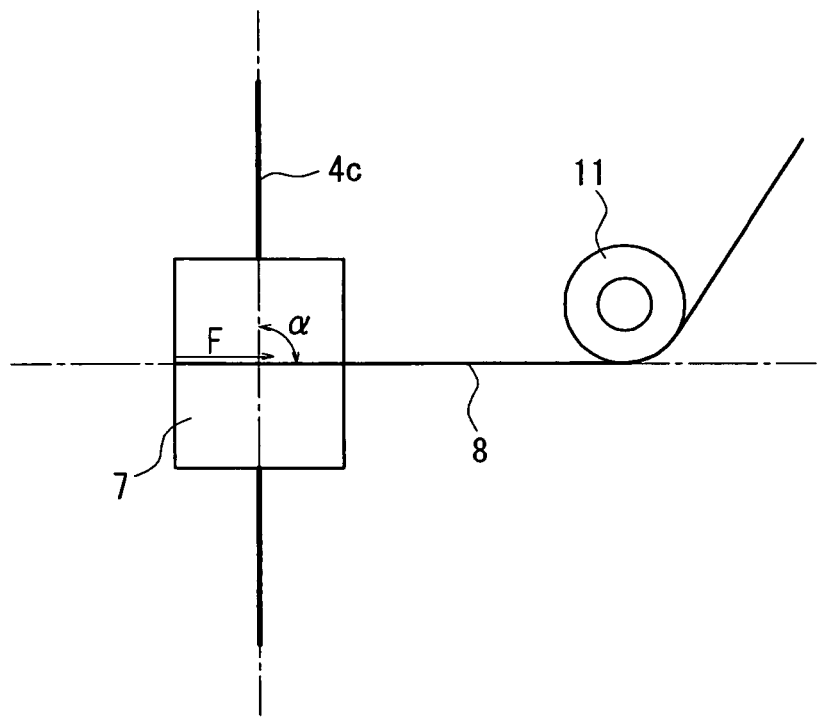
FIG. 4A is a schematic view for explaining a preferable example of the relationship between a rotation axis of a pulley and a direction in which a wire is moved, in the ultrasonic probe.
Figure 4B:
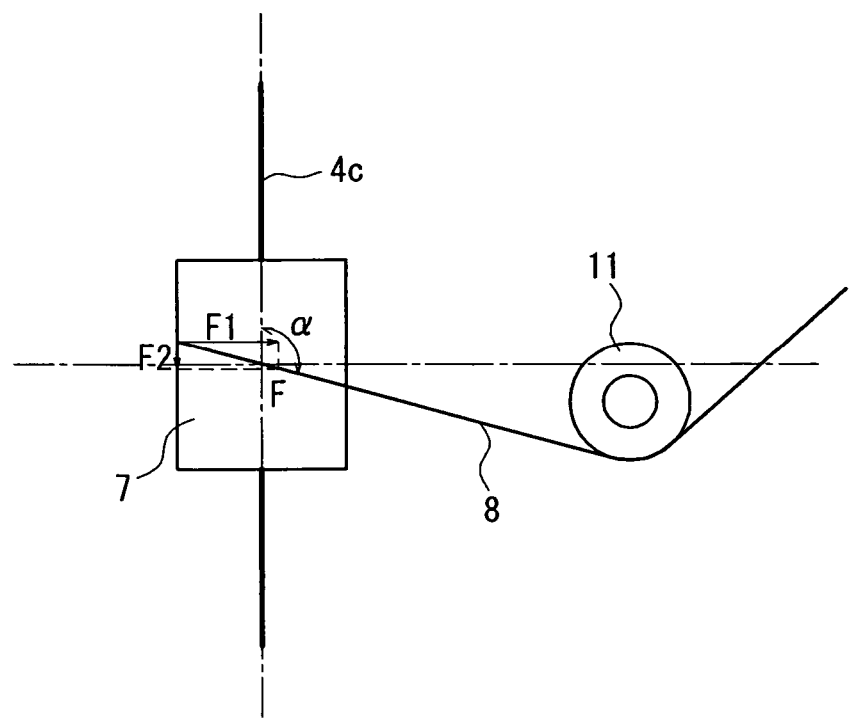
FIG. 4B is a schematic view showing another example of the relationship between the rotation axis of the pulley and the direction in which the wire is moved, in the ultrasonic probe.
Figure 5:
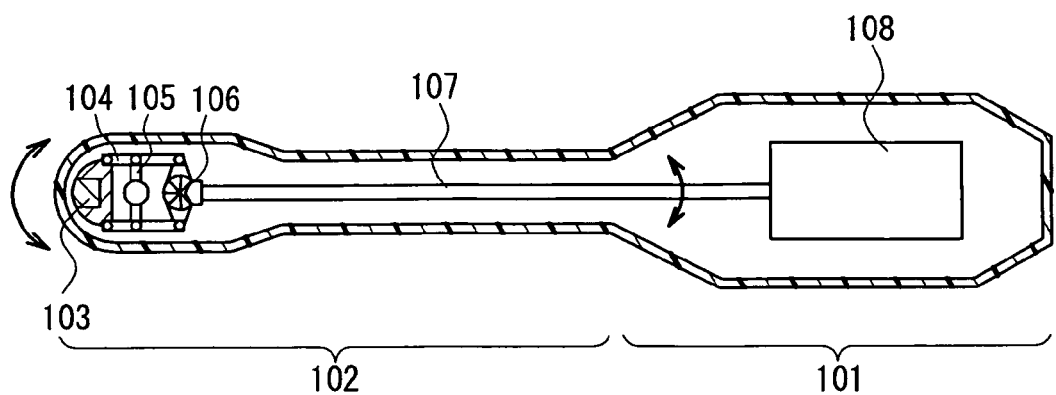
FIG. 5 is a schematic view showing a structure of an ultrasonic probe according to a first conventional example.
Figure 6:
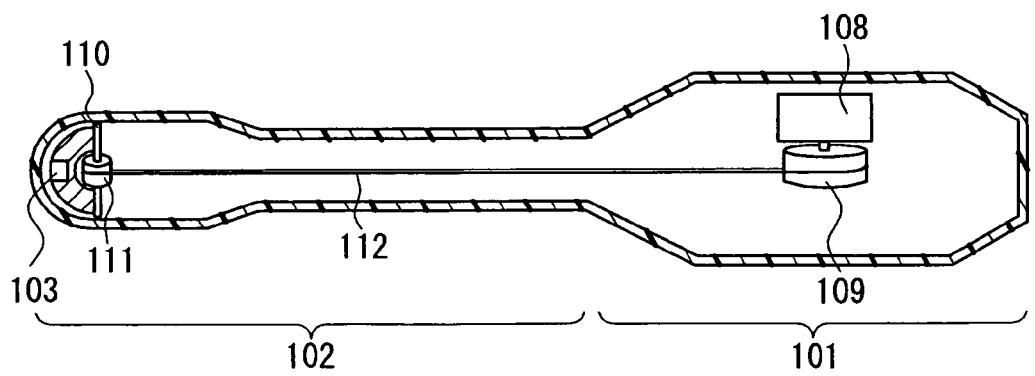
FIG. 6 is a schematic view showing a structure of an ultrasonic probe according to a second conventional example.

For example, as shown in FIG. 4B, in the case where the wire 8 is not moved in the direction orthogonal to the rotation axis 4c of the pulley 7 (an angle α in the figure is not 90 degrees), as a force (F) pulling the wire, a force (F2) in a direction parallel with the rotation axis 4c of the pulley is generated in addition to a force (F1) in the direction orthogonal to the rotation axis 4c of the pulley. When the force (F2) in the direction parallel with the rotation axis is generated, a phenomenon in which the wire slides in a direction of the rotation axis of the pulley on the peripheral surface of the pulley is likely to occur.

On the other hand, as shown in FIG. 4A, in the case where the wire 8 is moved in the direction orthogonal to the rotation axis 4c of the pulley 7 (an angle α in the figure is 90 degrees), the force in the direction parallel with the rotation axis of the pulley is not generated. Thus, it is possible to suppress sliding of the wire on the peripheral surface of the pulley.

The effect of suppressing wire sliding as mentioned above becomes higher as the angle between the rotation axis of the pulley and the movement direction of the wire is closer to 90 degrees. However, this angle need not necessarily be 90 degrees exactly but may be any angle within a range that allows wire sliding to be prevented or at least suppressed to an allowable level. Such a range of the angle depends on the pulley, a material of the wire, surface states thereof, and the like, and may be, for example, 90±10 degrees, and preferably, 90±5 degrees.

When the rotation axis of the first pulley 6 and the rotation axis of the second pulley 7 are not parallel with each other, in order to move the wire 8 in the direction orthogonal to the rotation axis of each of the pulleys, it is required to change the movement direction of the wire 8 between on the peripheral surface of the first pulley 6 and on the peripheral surface of the second pulley 7. In such a case, as shown in the figures, intermediate pulleys 10 and 11 for changing the movement direction of the wire 8 may be provided between the first pulley 6 and the second pulley 7.

Another method for suppressing wire sliding as mentioned above includes forming a wire groove extending in a peripheral direction on the peripheral surface of the pulley, and positioning the wire in the wire groove. When the formation of the wire groove and the conversion of the movement direction of the wire by the intermediate pulleys are used together, wire sliding can be prevented almost perfectly.

Next, an operation of the ultrasonic probe will be described.

When the motor 5 is driven, the rotational movement of the motor 5 is transmitted to the first pulley 6 via the shaft 9 so as to rotate the first pulley 6. The rotational movement of the first pulley 6 is transmitted to the second pulley 7 via the wire 8 so as to rotate the second pulley 7. At this time, the wire 8 is moved in the direction orthogonal to the rotation axis of the first pulley 6 on the first pulley 6, and changed in movement direction by the intermediate pulleys 10 and 11, and then moved in the direction orthogonal to the rotation axis of the second pulley 7 on the second pulley 7. In this manner, the movement around the rotation axis (i.e., shaft axis) of the first pulley 6 can be transmitted by converting the same into the movement around the rotation axis (i.e., support axis 4c) of the second pulley 7. In conjunction with the rotation of the second pulley 7, the transducer unit 4 is swung around the support axis 4c.

As described above, in the ultrasonic probe, since the ultrasonic transducer is swung by wire drive, contact between gear structures, which is a problem in the first conventional example, can be prevented and thus undesirable vibrations created when the swing mechanism is driven can be reduced. Further, since the driving force of the motor is transmitted to the pulley and the wire via the shaft instead of being transmitted directly, the wire can be made relatively short. As a result, loosening of the wire can be reduced and thus displacement of the ultrasonic transducer can be reduced.

Next, an example of an ultrasonic diagnostic apparatus using the above-described ultrasonic probe will be described. This ultrasonic diagnostic apparatus includes as main components an ultrasonic probe and an apparatus main body. The ultrasonic probe is the above-described ultrasonic probe according to the present embodiment. The apparatus main body includes a control part for driving the probe, a transmitting and receiving part for transmitting and receiving signals to and from the probe, an image formation part for creating images of an object based on the received signals, and an image display part for displaying a created tomogram.

An operation of the ultrasonic diagnostic apparatus will be described below. Initially, an operator holds the grip portion of the probe outside a body cavity, and inserts the inserting portion into the body cavity, so that the ultrasonic transducer housing portion is located in the vicinity of an object. Next, electric signals (transmitted signals) are transmitted from the transmitting and receiving part of the ultrasonic diagnostic apparatus to the ultrasonic probe. The transmitted signals are converted into ultrasonic waves in the ultrasonic transducer of the probe, and the converted ultrasonic waves are transmitted to the object. These ultrasonic waves are reflected by the object, and a part of the reflected waves is received and converted into electric signals (received signals) by the ultrasonic transducer. The converted received signals are transmitted to the transmitting and receiving part of the ultrasonic diagnostic apparatus. By performing the transmitting and receiving operation repeatedly while swinging the ultrasonic transducer in the probe, scanning of the ultrasonic waves can be carried out. The swing of the ultrasonic transducer is realized by driving the motor by a driving signal from the control part of the ultrasonic diagnostic apparatus and operating the swing mechanism of the probe as described above. Then, the received signals are subjected to various processes and then outputted to the image formation part, where ultrasonic images (tomogram or the like) of the object are created based on the received signals. The created ultrasonic images are outputted to the image display part.

According to the ultrasonic diagnostic apparatus, undesirable vibrations created when the swing mechanism is driven in the ultrasonic probe can be reduced. Therefore, smooth swing movement of the ultrasonic transducer, i.e., smooth ultrasonic scanning can be performed, which allows precise ultrasonic images to be obtained. Further, since loosening of the wire of the swing mechanism can be reduced in the ultrasonic probe, displacement of the ultrasonic transducer can be reduced, which allows precise ultrasonic images to be obtained.

INDUSTRIAL APPLICABILITY

As described above, according to the ultrasonic probe of the present invention, it is possible to realize smooth ultrasonic scanning of the ultrasonic transducer and to reduce displacement of the ultrasonic transducer. Thus, such an ultrasonic probe is suitable for use as a probe configuring an ultrasonic diagnostic apparatus in various fields of medicine.

The invention claimed is:

1. An ultrasonic probe, comprising:
   an inserting portion to be inserted into a body cavity; and
   a grip portion held by an operator outside of the body cavity,
   wherein the inserting portion includes a transducer unit for transmitting and receiving an ultrasonic wave, a rotation axis provided in the transducer unit, and a swing mechanism for swinging the transducer unit around the rotation axis as a center axis, and the grip portion includes a motor for driving the swing mechanism,
   the swing mechanism includes a shaft having a first end connected to the motor, a first pulley directly connected to a second end of the shaft a second pulley coaxially provided at the rotation axis, and a wire connecting the first pulley and the second pulley,
   the shaft is oriented such that its longitudinal direction is parallel to a longitudinal direction of the inserting portion,
   a length of the shaft is longer than a distance between the first pulley and the second pulley, and
   rotational movement of the motor is transmitted to the transducer unit via the shaft, the first pulley, the wire, and the second pulley.

2. The ultrasonic probe according to claim 1, wherein the first pulley and the second pulley have the same diameter.

3. The ultrasonic probe according to claim 1, wherein the wire is moved in a direction orthogonal to a direction of a rotation axis of the first pulley on a peripheral surface of the first pulley, and moved in a direction orthogonal to a direction of a rotation axis of the second pulley on a peripheral surface of the second pulley.

4. The ultrasonic probe according to claim 1,
   wherein the shaft and the transducer unit are provided so that a direction of a rotation axis of the shaft is orthogonal to a direction of the rotation axis of the transducer unit, and
   in the swing mechanism, the direction in which the wire is moved is changed perpendicularly between the first pulley and the second pulley.

5. The ultrasonic probe according to claim 4, wherein the swing mechanism includes a third pulley for changing perpendicularly the direction in which the wire is moved.

6. The ultrasonic probe according to claim 1, wherein a groove in which the wire is positioned is formed on the peripheral surface of the first pulley and the second pulley.

7. The ultrasonic probe according to claim 1, wherein the shaft extends from the motor for driving the swing mechanism into the inserting portion.

8. The ultrasonic probe according to claim 1, wherein the transducer unit is located on an extension of the shaft.

9. The ultrasonic probe according to claim 1, wherein the transducer includes a support axis that is coaxial with the rotation axis of the transducer unit, the second pulley being attached to the transducer unit through the support axis.

* * * * *

UNITED STATES PATENT AND TRADEMARK OFFICE
CERTIFICATE OF CORRECTION

| | | |
|---|---|---|
| PATENT NO. | : 8,083,681 B2 | Page 1 of 1 |
| APPLICATION NO. | : 10/534961 | |
| DATED | : December 27, 2011 | |
| INVENTOR(S) | : Kadokura | |

It is certified that error appears in the above-identified patent and that said Letters Patent is hereby corrected as shown below:

Column 7, line 26 (Claim 1): "...to a second end of the shaft a second pulley coaxially..." should read --...to a second end of the shaft, a second pulley coaxially...--

Signed and Sealed this
Tenth Day of July, 2012

David J. Kappos
*Director of the United States Patent and Trademark Office*